United States Patent [19]

Vandermark

[11] 3,949,234
[45] Apr. 6, 1976

[54] SMOKE DETECTOR DEVICE
[75] Inventor: James R. Vandermark, Agincourt, Canada
[73] Assignee: Lawrence Peska Associates, Inc., New York, N.Y. ; a part interest
[22] Filed: Aug. 26, 1974
[21] Appl. No.: 500,522

[52] U.S. Cl............. 250/573; 250/564; 340/237 S; 356/207
[51] Int. Cl.²........................................ G01N 21/12
[58] Field of Search .......... 250/564, 573, 576, 229; 356/201, 207, 208; 340/237 S

[56] References Cited
UNITED STATES PATENTS

| 2,042,095 | 5/1936 | Grant, Jr. | 250/573 X |
| 2,306,588 | 12/1942 | Cahusac et al. | 356/207 X |
| 2,763,853 | 9/1956 | Grant, Jr. | 340/237 S |
| 3,600,590 | 8/1971 | Einstein | 356/207 X |
| 3,826,577 | 7/1974 | Irwin | 250/573 X |

Primary Examiner—Archie R. Borchelt
Assistant Examiner—E. R. LaRoche

[57] ABSTRACT

A smoke detector device for detecting the density of smoke in a smoke passage, comprised of a light source, a photocell, a means for focusing a beam of light emitted from the light source across the smoke passage onto the photocell, and a circuit means coupled to the photocell and arranged to produce a signal when the smoke density in the smoke passage is above a specific smoke density level. The means for focusing the beam of light is comprised of a first lens and a second lens; the first lens is in optical communication with the light emitted from the light source and is constructed and positioned so as to focus the light across the smoke passage onto the second lens; the second lens is constructed and positioned so as to focus the light coming from the first lens onto the photocell. The smoke detector device may further have a first and second lens which are removable and a means for testing the signal.

9 Claims, 4 Drawing Figures

U.S. Patent   April 6, 1976   3,949,234
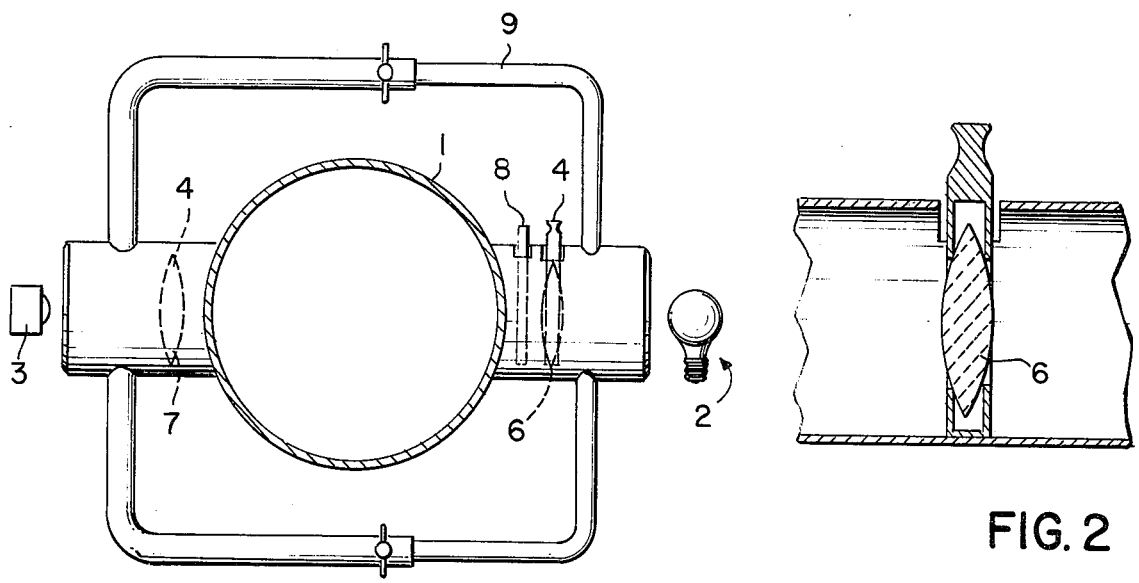
FIG. 1
FIG. 2
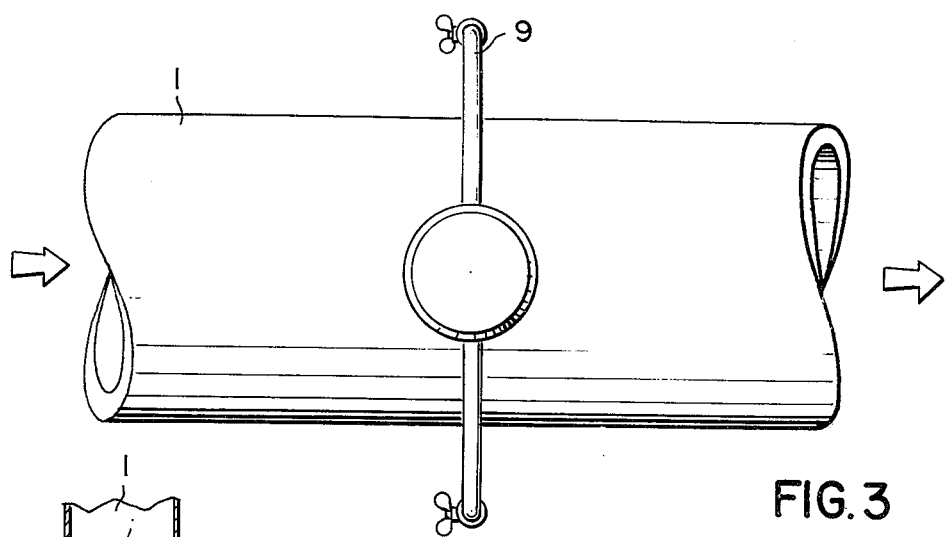
FIG. 3
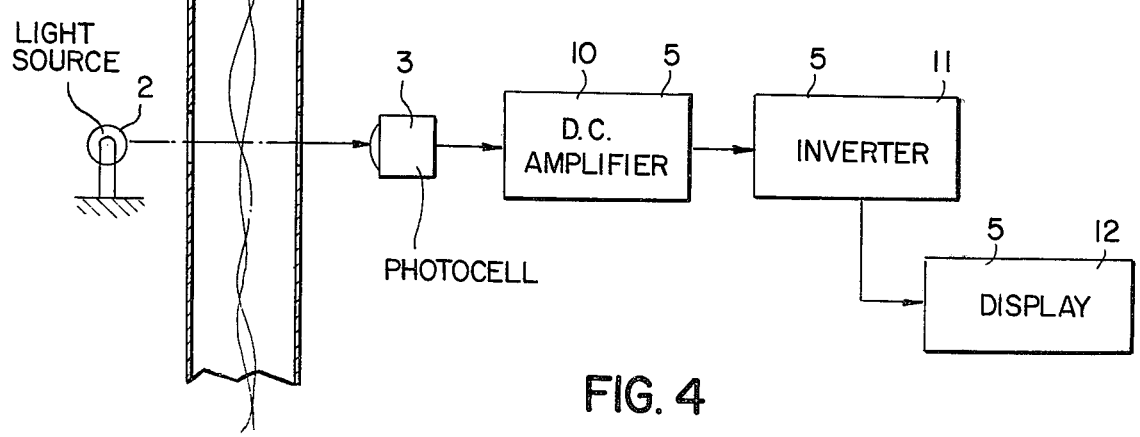
FIG. 4

SMOKE DETECTOR DEVICE

The present invention relates to a system for detecting smoke in a smoke passage, and more particularly to detecting a change in the density of the smoke in the smoke passage.

A variety of electronic devices have been developed for monitoring the level of smoke, vapor or other particles present in a room or enclosure to detect and call attention to abnormal conditions of combustion, and other abnormal conditions which may result from fires, explosions or other dangerous occurrences.

The present invention is intended to provide a smoke detector device for detecting the density of smoke in a smoke passage, comprised of a light source, a photocell, a means for focusing a beam of light emitted from the light source across the smoke passage onto the photocell, a circuit means coupled to the photocell and arranged to produce a signal when the smoke density in the smoke passage is above a specific smoke density level.

The present invention provides a simple and effective smoke detector in which the presence of smoke in the smoke passage or the change of density of smoke in the smoke passage partially obscures the beam of light, thereby causing a diminution in the light energy received by the cell. The resulting change in the electrical characteristics of the cell are detected by associated circuitry, i.e., a circuit means, and is employed to initiate an alarm indication when the smoke density in the smoke passage is above a specific smoke density level.

The principal object of the present invention, therefore, is to provide a novel and improved smoke detector device for detecting the density of smoke in a smoke passage.

Another object of this invention is to provide a smoke detector device which is simple and economical to manufacture, efficient to operate and durable to use.

Another object of this invention is to provide a smoke detector device which is easily removable and attachable from and to a smoke passage.

A still further object of this invention is to provide a smoke detector device in which the means for focusing the beam of light is easily removed from the smoke detector device for cleaning.

A still further object of this invention is to provide a smoke detector device having a means for easily testing the correctness of the signal produced by the photocell.

Other objects and advantages of the invention will be apparent from the following description and from the accompanying drawings which shown, by way of examples, embodiments of the invention.

IN THE DRAWINGS

FIG. 1 is a sectional view of a smoke passage having the new and novel smoke detector device attached to the smoke passage.

FIG. 2 is a sectional view of the removable lens used in the means for focusing the beam of light emitted from the light source.

FIG. 3 is a longitudinal view of the smoke passage with the new and novel smoke detector device attached thereto.

FIG. 4 is a schematic sectional view of the smoke detector device circuit means, light source, photocell and smoke passage.

Referring to the drawings more specifically there is shown a smoke detector device for detecting the density of smoke in a smoke passage 1. The smoke detector device is comprised of a light source 2, and a photocell 3. The device is further comprised of a means for focusing 4 a beam of light emitted from the light source across the smoke passage onto the photocell.

The device is still further comprised of a circuit means (5) coupled to the photocell and arranged to produce a signal when the smoke density in the smokepassage is above a specific smoke density level.

The means for focusing the beam of light may be comprised of a first lens 6 and a second lens 7. The first lens of the focusing means is in optical communication with the light emitted from the light source 2 and is constructed and positioned so as to focus the light across the smoke passage 1 onto the second lens 7. The second lens of the focusing means is constructed and positioned so as to focus the light coming from the first lens 6 onto the photocell 3.

The first and second lens may be removable from the smoke detector device for cleaning. FIG. 2 shows a lens with a means for removing the lens from the smoke detector device.

The smoke detector device may further be comprised of a means for testing the signal produced by the circuit means attached to the photocell 8.

For example, the means for testing the signal may be a block plate 8 slidably mounted in the smoke detector device. The block plate having a first position (as shown in FIG. 1) and a second position. The block plate is slidable between the first position and the second position. The block plate when used in the first position does not block the beam of light coming from the light source 2 onto the photocell 3. In effect, when the block plate is in the first position the smoke detector device is operating in a normal fashion. When the block plate is in the second position the block plate blocks the beam of light coming from the light source 2 onto the photocell and thus indicates a high density of smoke blocking the light to the photocell and thus activates the signal produced by the circuit means.

The block plate may be located in several positions along the path which the beam of light travels. For example, the block plate may be between the light source and the first lens, or between the first lens and the second lens, or between the second lens and the photocell.

The smoke detector device may further be comprised of an adjustable means 9 for detachably mounting the light source 2, the photocell 3, the means for focusing 4, and the means for testing the signal 8 on various size smoke passages 1. For example, the adjustable means for detachably mounting may be comprised of a circumferential support around the smoke passage 9.

The smoke detector device is further comprised of a circuit means. The circuit means will produce a signal from the electrical changes in the photocell. The circuit means, for example may be comprised of a DC amplifier 10 electrically coupled to the photocell 3 for amplifying the DC signal from the photocell. The circuit means may further have an inverter 11 electrically coupled to the DC amplifier and a display board 12 electrically coupled to the inverter 11 for displaying the signal.

In use smoke from the combustion of fuel, garbage, etc. will pass thru the smoke passage. During the combustion of the fuel, etc. the smoke density will change in relation to the efficiency of combustion. For example, when combustion efficiency is low, i.e., an insufficient quantity of oxygen for complete combustion, the smoke in the smoke passage will be heavy. The light source which emits a beam of light across the smoke passage will be partially blocked out by the heavier smoke density. The beam of light will thus be diminished in intensity on the photocell. The circuit means will thus transmit this change in smoke density to the display board by transmitting the change in voltage produced by the photocell to the display board.

The display board will have a signal on it which will indicate when a specific smoke density level is reached.

The smoke detector device may be calibrated to produce a signal when a predetermined smoke density level is reached.

The lenses in the focusing means may be removed from the smoke detector device for cleaning off particles of smoke collected on the lenses.

The block plate may be used to block out the beam of light to test the signal. The block plate may further have a film in it for calibrating the smoke detector device to a specific smoke density level.

The smoke detector device may further have an adjustable means for detachably mounting the smoke detector device from a smoke passage, and, for example, placing it on another size smoke passage. This invention contemplates the use of one smoke detector device which can be used on several sized smoke passages.

The lenses in the focusing means should be constructed of a high temperature material able to withstand the temperatures reached in the smoke passage, i.e., at least 1000°F.

The smoke detector device should be constructed of a light material, i.e., aluminum, etc., so that the smoke detector device may be easily removed from the smoke passage and attached to another smoke passage or transported from one place to another.

While the invention has been described and illustrated with reference to specific embodiments thereof, it will be understood that other embodiments may be resorted to without departing from the invention. For example, the positions of the source of light and of the circuit means may be varied and mirrors or other reflecting surfaces used to accomplish the results of the present construction. Therefore the forms of the invention set out above should be considered as illustrative and not as limiting the scope of the following claims.

Having thus described the invention, what is claimed as new is:

1. A smoke detector device for detecting density of smoke in various size smoke passages which is easily removable and circumferentially attachable to the various size smoke passages, comprised of:
   a. a light source;
   b. a photocell;
   c. a means for focusing a beam of light emitted from the light source across the smoke passage onto the photocell;
   d. a circuit means coupled to the photocell and arranged to produce a signal when the smoke density in the smoke passage is above a specific smoke density level;
   e. a means for testing the signal; and
   f. an adjustable means for detachably and circumferentially mounting the means for focusing and the means for testing the signal on the various size smoke passages wherein the mounting means is adjustable for mounting on various size smoke passages.

2. The smoke detector device of claim 1, wherein the circuit means is comprised of (a) a DC amplifier electrically coupled to the photocell for amplifying the DC signal from the photocell;
   b. an inverter electrically coupled to the DC amplifier;
   c. a display board electrically coupled to the inverter for displaying the signal.

3. The smoke detector device of claim 1, wherein the adjustable means for detachably mounting is comprised of a circumferential support around the smoke passage.

4. The smoke detector device of claim 3, wherein the circumferential support around the smoke passage is comprised of two circumferential mating members.

5. The smoke detector device of claim 1, wherein the means for focusing the beam of light is comprised of a first lens and a second lens; the first lens is in optical communication with the light emitted from the light source and is constructed and positioned so as to focus the light across the smoke passage onto the second lens, the second lens is constructed and positioned so as to focus the light coming from the first lens onto the photocell.

6. The smoke detector device of claim 5, wherein the first lens and the second lens are removable from the smoke detector device for cleaning.

7. The smoke detector device of claim 5, wherein the means for testing the signal, is a block plate slidably mounted in the smoke detector; the block plate having a first position and a second position and slidable between the first position and the second position; the block plate when in the first position does not block the beam of light coming from the light source onto the photocell; and wherein the block plate when in the second position does block the beam of light coming from the light source onto the photocell.

8. The smoke detector device of claim 7, wherein the block plate is slidably mounted between the first lens and the second lens.

9. The smoke detector device of claim 7, wherein the block plate is constructed of a film which approximates a specific smoke density level.

* * * * *